(12) United States Patent
Berrizbeitia et al.

(10) Patent No.: US 9,474,657 B2
(45) Date of Patent: Oct. 25, 2016

(54) ABSORBENT ARTICLES WITH BARRIER LEG CUFFS

(71) Applicant: The Procter & Gamble Company, Cincinnati, OH (US)

(72) Inventors: Jose Mauricio Berrizbeitia, Deerfield Township, OH (US); Ernesto Gabriel Bianchi, Oberursel (DE); Andrea Marie Frazer, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 231 days.

(21) Appl. No.: 14/247,402

(22) Filed: Apr. 8, 2014

(65) Prior Publication Data

US 2014/0303583 A1 Oct. 9, 2014

Related U.S. Application Data

(60) Provisional application No. 61/809,519, filed on Apr. 8, 2013.

(51) Int. Cl.
*A61F 13/15* (2006.01)
*A61F 13/49* (2006.01)
(Continued)

(52) U.S. Cl.
CPC ... *A61F 13/49009* (2013.01); *A61F 13/15699* (2013.01); *A61F 13/15739* (2013.01); *A61F 13/4942* (2013.01); *A61F 13/515* (2013.01); *A61F 2013/49092* (2013.01); *Y10T 156/10* (2015.01)

(58) Field of Classification Search
CPC .............. A61F 13/151; A61F 13/499; A61F 13/15699; A61F 13/15739; A61F 13/49009; A61F 13/4942; A61F 13/515; A61F 2013/49092
See application file for complete search history.

(56) References Cited

U.S. PATENT DOCUMENTS 3,848,594 A 11/1974 Buell
3,860,003 A 1/1975 Buell
(Continued)

FOREIGN PATENT DOCUMENTS

EP 0 149 880 A2 7/1985
EP 0 530 438 B1 2/1997
(Continued)

OTHER PUBLICATIONS

PCT International Searach Report mailed Jul. 22, 2014 (12 pages).

*Primary Examiner* — Bradley Philips
(74) *Attorney, Agent, or Firm* — Andrew J. Mueller (57) ABSTRACT

An absorbent article (20) for personal hygiene having a body-facing surface and an opposed garment-facing surface, the article having a front region (Z1), a back region (Z3) and an intermediate crotch region (Z2). The absorbent article comprises on each longitudinal side a gasketing cuff (32) and a barrier leg cuff (34) formed from the same web of nonwoven barrier material (110). The web of nonwoven barrier material is attached at least in the crotch region (Z2) to the topsheet by a plurality of mechanical and/or heat bonds (70), the plurality of mechanical and/or heat bonds defining in the crotch region a longitudinally extending bonding area (71) having a width W1. An adhesive (75) attaches in the crotch region the topsheet to the backsheet an that the adhesive covers at least 20% of the bonding area, this being also the case when the adhesive is notionally shifted laterally by any distance up to 4 mm.

13 Claims, 5 Drawing Sheets

(51) Int. Cl.
*A61F 13/494* (2006.01)
*A61F 13/515* (2006.01)

(56) References Cited

U.S. PATENT DOCUMENTS

| | | |
|---|---|---|
| 3,911,173 A | 10/1975 | Sprague |
| 3,929,135 A | 12/1975 | Thompson |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievit et al. |
| 4,573,986 A | 3/1986 | Minetola et al. |
| 4,609,518 A | 9/1986 | Curro et al. |
| 4,629,643 A | 12/1986 | Curro et al. |
| 4,662,875 A | 5/1987 | Hirotsu et al. |
| 4,681,793 A | 7/1987 | Linman et al. |
| 4,695,278 A | 9/1987 | Lawson |
| 4,699,622 A | 10/1987 | Toussant et al. |
| 4,704,116 A | 11/1987 | Enloe |
| 4,710,189 A | 12/1987 | Lash |
| 4,738,677 A | 4/1988 | Foreman |
| 4,785,996 A | 11/1988 | Ziecker et al. |
| 4,795,454 A | 1/1989 | Dragoo |
| 4,808,178 A | 2/1989 | Aziz et al. |
| 4,840,692 A * | 6/1989 | Kamstrup-Larsen . A61F 5/4401 156/252 |
| 4,842,666 A | 6/1989 | Werenica |
| 4,846,815 A | 7/1989 | Scripps |
| 4,894,060 A | 1/1990 | Nestegard |
| 4,909,803 A | 3/1990 | Aziz et al. |
| 4,946,527 A | 8/1990 | Battrell |
| 4,963,140 A | 10/1990 | Robertson et al. |
| 5,006,394 A | 4/1991 | Baird |
| 5,137,537 A | 8/1992 | Herron et al. |
| 5,151,092 A | 9/1992 | Buell et al. |
| 5,221,274 A | 6/1993 | Buell et al. |
| 5,242,436 A | 9/1993 | Weil et al. |
| 5,269,234 A | 12/1993 | Powell |
| 5,281,683 A | 1/1994 | Yano et al. |
| 5,433,715 A | 7/1995 | Tanzer et al. |
| 5,499,978 A | 3/1996 | Buell et al. |
| 5,506,324 A | 4/1996 | Gartner et al. |
| 5,507,736 A | 4/1996 | Clear et al. |
| 5,532,323 A | 7/1996 | Yano et al. |
| 5,549,791 A | 8/1996 | Herron et al. |
| 5,554,145 A | 9/1996 | Roe et al. |
| 5,571,096 A | 11/1996 | Dobrin et al. |
| 5,574,121 A | 11/1996 | Irie et al. |
| 5,580,411 A | 12/1996 | Nease et al. |
| 5,591,152 A | 1/1997 | Buell et al. |
| 5,599,335 A | 2/1997 | Goldman et al. |
| 5,607,414 A | 3/1997 | Richards et al. |
| 5,607,760 A | 3/1997 | Roe |
| 5,609,587 A | 3/1997 | Roe |
| 5,643,588 A | 7/1997 | Roe et al. |
| 5,700,254 A | 12/1997 | McDowall et al. |
| H1732 H | 6/1998 | Johnson |
| 5,837,789 A | 11/1998 | Stockhausen et al. |
| 5,865,823 A | 2/1999 | Curro |
| 5,938,648 A | 8/1999 | LaVon et al. |
| 5,968,025 A | 10/1999 | Roe et al. |
| 5,980,500 A * | 11/1999 | Shimizu ............... A61F 13/539 604/358 |
| 6,004,306 A | 12/1999 | Robles et al. |
| 6,143,821 A | 11/2000 | Houben |
| 6,432,098 B1 | 8/2002 | Kline et al. |
| 6,534,149 B1 | 3/2003 | Daley et al. |
| 6,645,569 B2 | 11/2003 | Cramer et al. |
| 6,716,441 B1 | 4/2004 | Osborne et al. |
| 6,863,933 B2 | 3/2005 | Cramer et al. |
| 6,946,585 B2 | 9/2005 | London Brown |
| 6,979,564 B2 | 12/2005 | Glucksmann et al. |
| 6,987,153 B2 | 1/2006 | Diehl et al. |
| 7,112,621 B2 | 9/2006 | Rohrbaugh et al. |
| 7,189,219 B1 | 3/2007 | Kasai et al. |
| 7,199,211 B2 | 4/2007 | Popp et al. |
| 7,250,481 B2 | 7/2007 | Jaworek et al. |
| 7,652,111 B2 | 1/2010 | Hermeling et al. |
| 7,687,596 B2 | 3/2010 | Hermeling et al. |
| 7,744,576 B2 | 6/2010 | Busam et al. |
| 7,750,203 B2 | 7/2010 | Becker et al. |
| 7,772,420 B2 | 8/2010 | Hermeling et al. |
| 7,786,341 B2 | 8/2010 | Schneider et al. |
| 7,838,722 B2 | 11/2010 | Blessing et al. |
| 8,205,066 B2 | 6/2012 | Brewer et al. |
| 8,206,533 B2 | 6/2012 | Hundorf et al. |
| 8,236,715 B2 | 8/2012 | Schmidt et al. |
| 8,287,999 B2 | 10/2012 | Schmidt et al. |
| 8,530,722 B2 | 9/2013 | Rinnert et al. |
| 2002/0123728 A1 | 9/2002 | Graf |
| 2003/0120248 A1 | 6/2003 | Miyamoto |
| 2003/0148684 A1 | 8/2003 | Cramer et al. |
| 2005/0008839 A1 | 1/2005 | Cramer et al. |
| 2005/0165208 A1 | 7/2005 | Popp et al. |
| 2005/0215155 A1 | 9/2005 | Young et al. |
| 2005/0234410 A1 | 10/2005 | Ashton et al. |
| 2005/0234411 A1* | 10/2005 | Ashton ............... A61F 13/4942 604/358 |
| 2007/0093767 A1 | 4/2007 | Carlucci et al. |
| 2007/0118087 A1 | 5/2007 | Flohr et al. |
| 2008/0091159 A1 | 4/2008 | Carlucci et al. |
| 2008/0312617 A1 | 12/2008 | Hundorf et al. |
| 2008/0312622 A1 | 12/2008 | Hundorf et al. |
| 2008/0312628 A1* | 12/2008 | Hundorf ............ A61F 13/15658 604/378 |
| 2009/0209931 A1* | 8/2009 | Wurster ............ A61F 13/15699 604/367 |
| 2009/0318884 A1 | 12/2009 | Meyer et al. |
| 2011/0196332 A1* | 8/2011 | Cheng ............... A61F 13/4942 604/385.24 |
| 2011/0250413 A1 | 10/2011 | Lu et al. |
| 2011/0268932 A1 | 11/2011 | Catalan et al. |
| 2011/0319848 A1 | 12/2011 | McKiernan et al. |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2014/0005622 A1 | 1/2014 | Wirtz et al. |

FOREIGN PATENT DOCUMENTS

| | | |
|---|---|---|
| WO | WO 90-15830 A1 | 12/1990 |
| WO | WO 95-16746 A1 | 12/1995 |
| WO | WO 95-34329 A1 | 12/1995 |
| WO | WO 2009-155265 A2 | 12/2009 |

* cited by examiner

ABSORBENT ARTICLES WITH BARRIER LEG CUFFS

FIELD OF THE INVENTION

The invention relates to personal hygiene absorbent articles for wearing in the lower torso, such as but not limited to baby diapers, training pants, adult incontinence products or sanitary napkins, comprising barrier leg cuffs. More particularly, the invention relates to improved attachment of the barrier leg cuffs to the rest of the article.

BACKGROUND OF THE INVENTION

Absorbent articles for personal hygiene, such as disposable diapers for infants, training pants for toddlers or adult incontinence undergarments are designed to absorb and contain body exudates, in particular large quantity of urine. These absorbent articles comprise several layers providing different functions, for example a topsheet, a backsheet and an absorbent core, among other layers. Absorbent articles should be able to absorb a large amount of fluid while preventing the fluid from leaking.

These absorbent articles may typically comprise elasticized containment elements at their longitudinal sides that help maintaining the article in contact with the body. Thus it usual for modern diaper to comprise raised flaps, typically referred to as barrier leg cuffs (or more simply "barrier cuffs") which improve the containment of fluid in the leg-torso joint regions. Each barrier leg cuff may typically comprise one or more elastic strings but some simpler articles have barrier leg cuffs which are not elasticized. Another type of containing elements commonly found in diapers is referred to as gasketing cuffs. Gasketing cuffs typically comprise one or more elastic string or elasticized element inserted in the chassis of the diaper, for example between the topsheet (and/or an extension of the barrier leg cuff material) and the backsheet, in the area of the leg openings to provide an effective seal while the diaper is in use.

Many patents have proposed improvement to these containment elements. For example U.S. Pat. No. 4,808,178 and U.S. Pat. No. 4,909,803 (Aziz) describe disposable diapers having such raised elasticized flaps referred to herein as barrier leg cuffs. U.S. Pat. No. 4,695,278 (Lawson) and U.S. Pat. No. 4,795,454 (Dragoo) describe disposable diapers having dual cuffs, including gasketing cuffs and barrier leg cuffs. U.S. Pat. No. 4,704,116 (Enloe) discloses an absorbent garment comprising a pair of gasketing cuffs and a pair of barrier leg cuffs which attached to or formed from the topsheet and spaced inwardly from said elasticized leg openings, defining a waste-containment pocket.

Different solutions have been proposed to attach the barrier leg cuffs to the chassis of the diapers. U.S. Pat. No. 4,795,454 (Dragoo) teaches attachment means such as an adhesive or heat/pressure sealing, ultrasonic bonding. Seal means such as an adhesive bead are further provided to present a barrier to the wicking of liquids through the topsheet. The seal means are said to prevent liquids from wicking underneath the barrier leg cuffs to the edges of the diaper. The seal means are positioned more inwardly of the diaper than the attachment means. U.S. Pat. No. 7,189,219 (Kasai) discloses creating liquid shut-off regions between the leg cuffs and the topsheet using a heat-seal.

The use of adhesive to attach the barrier leg cuffs to the rest of the article may however increase costs, be less environmentally friendly, and adhesive can come in contact with the wearer's skin. It has also been proposed to attach the barrier leg cuffs to the rest of the absorbent article using mechanical and/or heat bonding. Although this has the advantage of not requiring the use of adhesive, it has however the drawback that undesired holes may be pierced through the bonded materials while joining them. The unwanted holes thus formed may compromise the liquid restraining function of the barrier leg cuffs. The inventors have found that this is especially a problem for materials having a relatively low combined basis weight of less than 60 gsm and/or having a large basis weight variation. US 2011/0196332 (Cheng) addresses partially this problem by suggesting a new barrier leg cuff material comprising two nonwoven component layers, one component layer comprising fibers having a number-average diameter less than about 1 micron, and having a local basis weight variation of less than about 10%. However this material may be more complex and costly to manufacture than conventional nonwoven barrier material, and while reducing the number and size of holes, it does not completely eliminate their occurrence.

Although the prior art has suggested many technical solutions, there is still a need for a simple and cost-effective way to make and attach barrier leg cuffs to the rest of the absorbent article without disrupting their barrier function in the area of bonding. The present inventors are now suggesting a simple and cost effective way to solve this problem.

SUMMARY OF THE INVENTION

The invention relates to an absorbent article for personal hygiene and a method for making such an absorbent article as indicated in the claims. The absorbent article has a body-facing surface and an opposed garment-facing surface, and can be notionally divided in a front region, a back region and an intermediate crotch region. The regions are of equal length as measured along the longitudinal axis of the article. The article comprises a liquid pervious topsheet, a liquid impervious backsheet, an absorbent core disposed between the topsheet and the backsheet.

The article comprises on each of its longitudinal sides a barrier leg cuff having a free distal edge and optionally an elastic element for spacing the distal edge away from the body-facing surface of the absorbent article so as to cause the barrier leg cuff to stand up, and an elastically contractible gasketing cuff disposed adjacent the longitudinal edge of the absorbent article. The gasketing cuff and the barrier leg cuff are at least partially formed from the same web of nonwoven barrier material extending at least from the distal edge of the barrier leg cuff to the longitudinal side edge of the article.

The web of nonwoven barrier material is at least attached to the topsheet in the crotch region of the article by a plurality of mechanical and/or heat bonds. The plurality of mechanical and/or heat bonds defines in the crotch region a longitudinally extending bonding area having a width W1. The absorbent article further comprises at least in the crotch region an adhesive at least partially attaching the topsheet to the backsheet. The adhesive may be advantageously laterally centered on the bonding area. The adhesive covers at least 20% of the bonding area, this being also the case when the adhesive application area is notionally shifted laterally by any distance up to 4 mm.

The function of the adhesive may be twofold. First, it may provide an attachment of the backsheet to the topsheet/barrier cuff composite along the longitudinal sides of the article, thus providing a proximal edge for the barrier leg cuffs to stand up. Second, the inventors have found that the holes, which may be present within the mechanical and/or heat bonds, can be effectively sealed by the adhesive. Through this adhesive seal, side leakage caused by the micro-holes can be efficiently prevented.

However, the inventors have found that even in the case when up to 100% of the bonding zone is covered by the adhesive, side leakages through the barrier leg cuffs can still take place. After investigation leading to this invention, the inventors have found that even on modern machine a tolerance, or shift, of the adhesive application area of up to 4 mm relative to the bonding area is possible in the lateral direction. Thus for example if the bonding zone had a width of 3 mm, and the adhesive is applied as a single line having a width of also 3 mm laterally centered on the bonding zone, the adhesive covers in theory 100% of the bonding area. However due to the lateral tolerance which may be up to 4 mm, in this example, the adhesive may cover less than 20% the bonding area, and possibly even 0%.

The inventors have thus found that it was important that, at least in the crotch region, the adhesive covers at least 20% of the bonding area when laterally centered on the bonding area but also when the adhesive application area is notionally shifted laterally by any distance up to 4 mm. This coverage can be achieved using different adhesive application patterns, a few of which will be exemplified in the following.

DETAILED DESCRIPTION OF THE INVENTION

Introduction

As used herein, the term "absorbent article for personal hygiene", or more simply "absorbent article" or "article" refers to disposable devices such as infant or adult diapers, training pants, and the like which are placed against or in proximity to the body of the wearer to absorb and contain the various exudates discharged from the body. The absorbent articles of the invention will be further illustrated in the below description and in the Figures in the form of a taped diaper. Nothing in this description should be however considered limiting the scope of the claims unless explicitly indicated otherwise. It is in particular considered that the invention may be used in training pants, adult incontinence products or some feminine hygiene articles. Unless indicated otherwise, the description refers to the dry article, re before use and conditioned at least 24 hours at 21° C.+/−2° C. and 50+/−20% Relative Humidity (RH).

A "nonwoven web" as used herein means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunhonding, solvent spinning, electrospinning, carding and airlaying. The basis weight of nonwoven webs is usually expressed in grams per square meter ($g/m^2$ or gsm).

The term "joined" or "bonded" or "attached", as used herein, encompasses configurations whereby an element is directly secured to another element by affixing the element directly to the other element, and configurations whereby an element is indirectly secured to another element by affixing the element to intermediate member(s) which in turn are affixed to the other element.

"Comprise," "comprising," and "comprises" are open ended terms, each specifies the presence of what follows, e.g., a component, but does not preclude the presence of other features, e.g., elements, steps, components known in the art, or disclosed herein. These terms based on the verb "comprise" should be read as encompassing the narrower terms "consisting of" which excludes any element, step, or ingredient not specified and "consisting essentially of" which limits the scope of an element to the specified materials or steps and those that do not materially affect the way the element performs its function. Any preferred or exemplary embodiments described below are not limiting the scope of the claims, unless specifically indicated to do so. Likewise, the words "typically", "normally", "advantageously" and the likes also qualify elements which are not intended to limit the scope of the claims unless specifically indicated to do so.

General Description of the Absorbent Article 20

Figure 1:
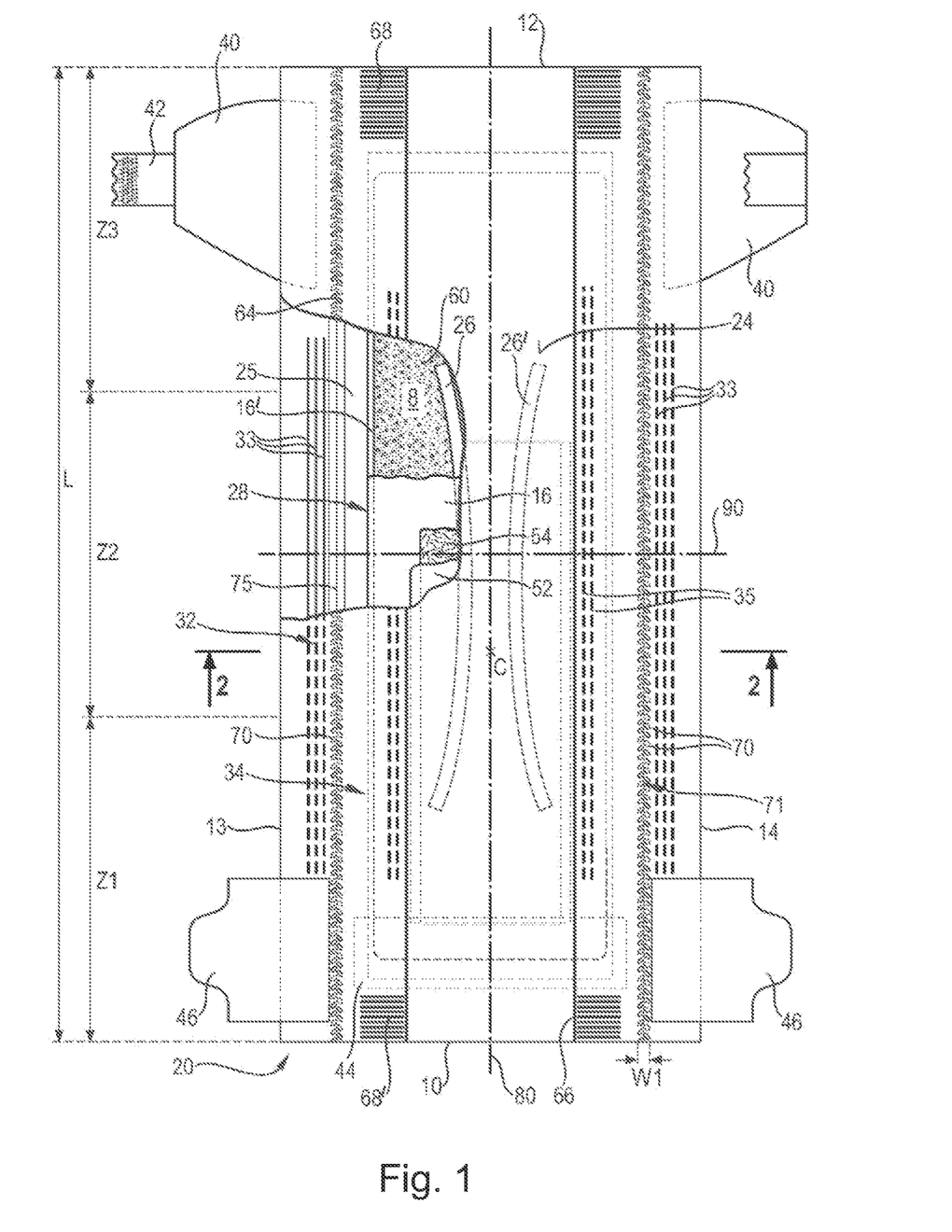
FIG. 1 shows a top view of an exemplary embodiment of the invention in the form of a taped diaper in a flattened form.

The absorbent article may be generally illustrated by an exemplary absorbent article according to the invention in the form of a baby diaper. FIG. 1 is a plan view of such an exemplary diaper 20 in a flattened state, which can be obtained by pulling the diaper and holding it taut on a flat surface, with portions of the structure being cut-away to more clearly show the construction of the diaper. This diaper 20 is shown for illustration purpose only, as the invention may be used for making a wide variety of diapers or other absorbent articles, such as training pant for example.

The absorbent article comprises a liquid permeable topsheet 24, a liquid impermeable backsheet 25, an absorbent core 28 between the topsheet 24 and the backsheet 25 and on each longitudinal side, a barrier leg cuff 34 and an elasticized gasketing cuff 32. The absorbent article may optionally comprise an acquisition-distribution system 50 ("ADS"), which in the example represented comprises a distribution layer 54 and an acquisition layer 52.

The absorbent article may also comprise typical taped diaper components such as a fastening system comprising adhesive tabs 42 attached towards the back edge of the article and cooperating with a landing zone 44 on the front of the article. The absorbent article may also comprise other typical elements, which are not represented, such as a back elastic waist feature, a front elastic waist feature, transverse barrier leg cuff(s), a lotion application, etc. . . . .

The absorbent article may be preferably thin. The caliper at the crotch point C of the article may be for example from 4.0 mm to 12.0 mm, in particular from 6.0 mm to 10.0 mm, as measured with a circular foot having a diameter of 20 mm (±0.2 mm) at a pressure of 2.07 kPa (0.30 psi).

The absorbent article of the invention may comprise a front edge 10, a back edge 12, and two longitudinal side edges 13, 14. The front edge 10 is the edge of the article which is intended to be placed towards the front of the user when worn, and the back edge 12 is the opposite edge. In a taped diaper, as exemplarily shown in FIG. 1, the back edge of the diaper is typically on the side of the diaper that comprises the fastening tabs 42 and the front edge is typically on the side of the diaper that comprise the matching landing zone 44. More generally, the front of the article has typically more absorbent capacity than the back of the article. The absorbent article, may be notionally divided by a longitudinal axis 80 extending from the front edge to the back edge of the article and dividing the article in two longitudinal sides substantially symmetrical relative to this axis, when the article is placed flat and viewed from above as in FIG. 1. The length L of the article can be measured along the longitudinal axis 80 from front edge 10 to back edge 12. The length of a training pant may be more easily measured after cutting the side seams of the pants in order to be able to flatten the pant. The terms "lateral" or "laterally" refers to the direction perpendicular to the longitudinal axis 80 and parallel to the lateral axis 90, that is left or right of the diaper as seen as orientated in FIG. 1.

The article can be notionally divided in three regions, a front region Z1 towards the front edge of the article, a back region Z3 towards the back edge of the article and an intermediate crotch region Z2 in-between, each having a length which is one third of L as measured along the longitudinal axis. A crotch point C can also be defined herein as the point placed on the longitudinal axis at a distance of two fifth (⅖) of L starting from the front edge 10 of the article 20.

The article comprises on each of its longitudinal sides a barrier leg cuff 34 and an elastically contractible gasketing cuff 32 disposed adjacent to a longitudinal edge of the absorbent article. The construction of the barrier leg cuff and the gasketing cuff will now be further detailed.

Barrier Leg Cuffs 34 and Gasketing Cuffs 32

The absorbent article comprises on each of its longitudinal side a barrier leg cuff 34 and a gasketing cuff 32. Each barrier leg cuff is delimited by a free standing distal edge 66 and is attached to rest of the article at least by a plurality of mechanical and/or heat bonds 70 at a so-called proximal edge. An elastic element 35 within the barrier leg cuffs can advantageously be present for spacing the distal edge away from the body-facing surface of the article on that the barrier leg cuffs can stand up when worn by the user. The elastic element can be for example one, two or more strands of elastic material 35 attached in a fold formed by the nonwoven barrier material 110 towards the distal edge (the fold may be maintained for example using an adhesive and/or mechanical bonds, as is usual in the art). The barrier leg cuffs can provide improved containment of liquids and other body exudates approximately at the junction of the torso and legs of the wearer.

The elastically contractible gasketing cuffs 32 are typically placed further towards the longitudinal edges of the article than the barrier leg cuffs 34. Thus the mechanical and/or heat bonds 70 may be placed between the gasketing cuff and the barrier leg cuff. Each gasketing cuff may comprise one, two, three or more elastic string or elastic element 33 comprised in the chassis of the diaper, as is known in the art. The gasketing cuffs can typically provide a better seal around the thighs of the wearer.

According to the invention, the barrier leg cuff and the gasketing cuff on each longitudinal side of the article are at least partially formed from the same web of nonwoven barrier material 110 which extends at least from the distal edge 66 of the barrier leg cuff to the respective longitudinal side edge 12, 14 of the article. The nonwoven barrier material may be any conventional and commercially available nonwoven suitable for this use, in particular a substantially liquid impervious material. Typical material may be selected from commercially available SMS nonwoven or SMMS nonwoven material (laminates of Spunbond (S) and Meltblown (M) layers). The nonwoven material may also comprise a nonwoven component layer comprising having fine fibers ("N-fibers") with an average diameter of less than 1 micron. Such a N-fiber layer may be added to, or otherwise incorporated with, other nonwoven component layers to form a nonwoven web of material. In some embodiments, the N-fiber layer may be used to produce a SNS nonwoven web or SMNS nonwoven web, for example.

The nonwoven barrier material may for example comprise a first nonwoven component layer comprising fibers having an average diameter in the range of about 8 microns to about 30 microns, a second nonwoven component layer comprising fibers having a number-average diameter of less than about 1 micron, a mass-average diameter of less than about 1.5 microns, and a ratio of the mass-average diameter to the number-average diameter less than about 2, and a third nonwoven component layer comprising fibers having an average diameter in the range of about 8 microns to about 30 microns. The second nonwoven component layer is disposed intermediate the first nonwoven component layer and the third nonwoven component layer.

The N-fibers may be comprised of a polymer, e.g., selected from polyesters, including PET and PBT, polylactic acid (PLA), alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types of Kraton), polystyrenes, polyamides, PHA (polyhydroxyalkanoates) and e.g. PHB (polyhydroxubutyrate), and starch-based compositions including thermoplastic starch, for example. The above polymers may be used as homopolymers, copolymers, e.g., copolymers of ethylene and propylene, blends, and alloys thereof. The N-fiber layer may be bonded to the other nonwoven component layers by any suitable bonding technique, such as the calender bond process, for example, also called thermal point bonding.

In some embodiments, the use of an N-fiber layer in a nonwoven web may provide a low surface tension barrier that is as high as other nonwoven webs that have been treated with a hydrophobic coating or a hydrophobic melt-additive, and still maintain a low basis weight (e.g., less than 15 gsm or, alternatively, less than 13 gsm). The use of the N-fiber layer may also provide a soft and breathable (i.e., air permeable) nonwoven material that, at least in some embodiments, may be used in single web layer configurations in applications which previously used double web layer configurations. Furthermore, in some embodiments, the use of the N-fiber layer may at least reduce the undesirable migration of hydrophilic surfactants toward the web and, therefore, may ultimately result in better leak protection for an associated absorbent article. Also, when compared to an SMS web having a similar basis weight, the use of a nonwoven web comprising the N-fiber layer may decrease the number of defects holes or pinholes through the mechanical bond site) created during the mechanical bonding process. N-fibers are further discussed in WO 2005/095700 and US2011/0196332 (Cheng).

Figure 2:
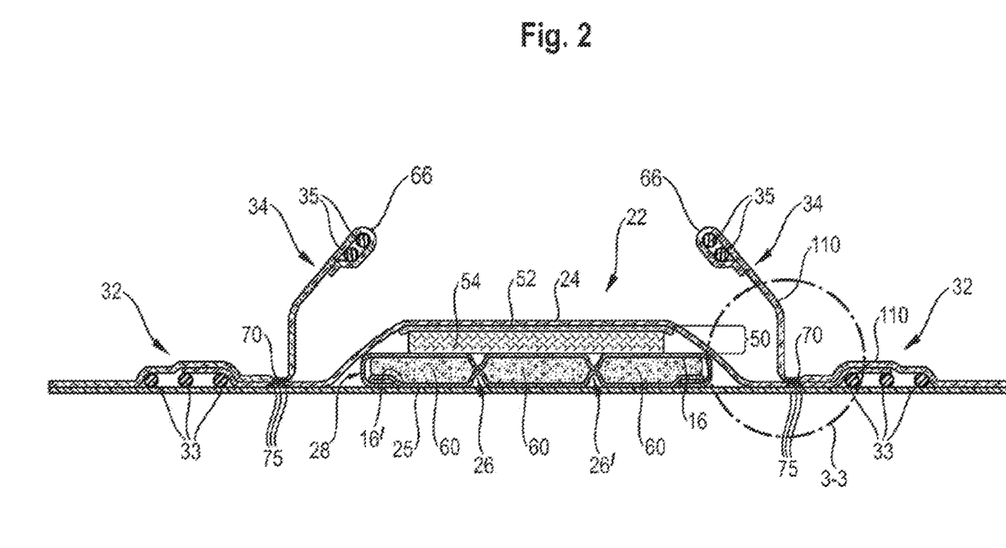
FIG. 2 shows a cross-section of the embodiment of FIG. 1.
Figure 3:
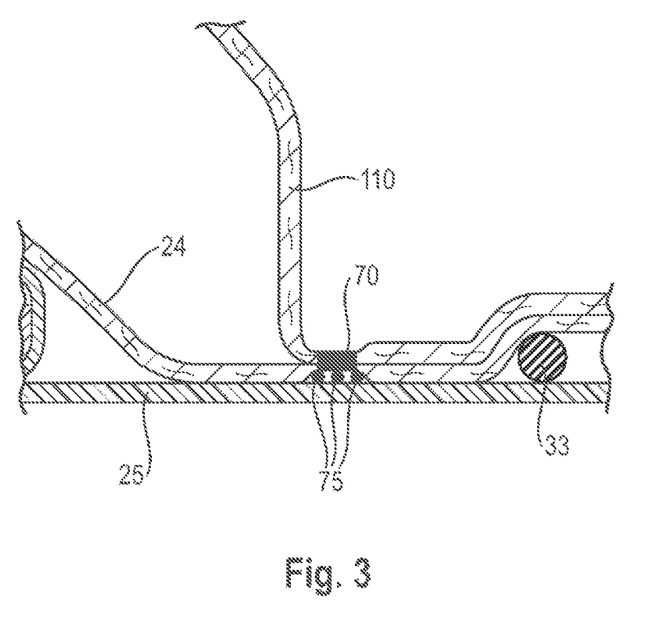
FIG. 3 shows a close-up view of the cross-sectional view of FIG. 2 comprising the bonding area and the adhesive.

The nonwoven barrier material may in particular be hydrophobic so as to provide a barrier function against leakage of the fluid from the topsheet towards the legs of the wearer. This is particular advantageous to provide a good barrier function when the nonwoven barrier material extends up to the longitudinal side edge of the article. The nonwoven barrier material may be directly attached or positioned face to face with the backsheet along the longitudinal side edges of the article, as shown in FIG. 2. In this way, the topsheet does not extend to the longitudinal side edge of the article which further reduces the risk of fluid leakage. In general, the nonwoven materials are typically made of polymers which are inherently hydrophobic (e.g. PE, PP, PET) and are not treated by surfactant to make them hydrophilic.

All or a portion of the barrier leg cuffs and/or gasketing cuffs may also be treated and/or coated with a lotion comprising an hydrophobic material such a petrolatum, which can increase the barrier function of the cuffs as well as provide skin benefits.

Mechanical and/or Heat Bonds 70

The web of nonwoven barrier material 110 is attached at least in the crotch region Z2 of the article to the topsheet by a plurality of mechanical and/or heat bonds 70. The term "mechanical and/or heat bond" refers to a bond formed between two or more materials by pressure (for example as disclosed in US2011/0196332A1), ultrasonic attachment, calendaring and other mechanical bonding processes, with or without the intentional application of heat, as well as heat bonding (also called "fusion" or "thermal" bonding). In particular the term covers bonds formed between fibers of one or more nonwoven(s) by the combination of pressure and temperature such that the polymers within the bond melt together to form a continuous film-like material. The term "mechanical and/or heat bond" however does not comprise a bond formed solely by an adhesive.

Figure 4:
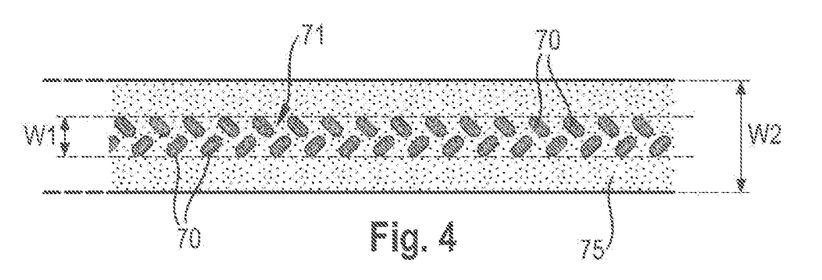
FIG. 4 shows a top view of an exemplary bonding area and the adhesive application area with the other layers removed for clarity.

The individual bonds may be of any shape, in particular circular or ovoid. As illustrated in FIG. 4 and following, the mechanical and/or heat bonds 70 may be of ovoid shape with their longer axis aligned at an angle of from about 20° to about 80° relative to the longitudinal direction of the article. The bonds may also be staggered in chevrons along two parallel lines along the longitudinal direction of the article.

The plurality of mechanical and/or heat bonds 70 defines in the crotch region a longitudinally orientated bonding area 71. The bonding area 71 is defined herein as the smallest rectangular area which encompasses the plurality of mechanical and/or heat bonds 70 in the crotch region. Thus the bonding area 71 comprises the bonds 70 and the regions between the bonds. The bonding area 71 has a width W1. The mechanical and/or heat bonds may typically extend further than the crotch region Z2 into the front region Z1 and back region Z3. The bonding area thus typically extends through the whole of the crotch region of the article. The bonding pattern may typically remain constant along the length of the bonding area. If this was not the case, the width W1 is defined as the maximum width of the bonding area formed by the bonds in the crotch region of the article. Typically, the width W1 may be from 0.5 mm to 10 mm, in particular between 0.5 mm to 8 mm, for example 3 mm.

The web of nonwoven barrier material 110 may extend longitudinally along the whole length of the article. The distal edge of the barrier leg cuffs may also be "tack bonded" to the topsheet a few centimeters from the front edge and back edge of the article, as represented in FIG. 1, so that in these sections the barrier leg cuff material remains flush with the topsheet. The tack bonds 68, 68' may be for example formed by adhesives and/or mechanical bonding.

Adhesive 75

The absorbent article further comprises an adhesive attaching at least in the crotch region Z2 of the article, the barrier nonwoven material 110 to the backsheet 25. The adhesive covers at least 20% m in particular at least 25%, 30%, 40%, 50% or up to 100% of the bonding area. The inventors have however found that a percentage of coverage below 100% may be also sufficient. The adhesive may thus for example cover from 20% to 75% of the bonding area, in particular from 30% to 50%. The adhesive may be advantageously laterally centered with the bonding area.

The adhesive may be any conventional adhesive used in the art, for example a hotmelt adhesive. Example of commercial adhesive is available from Fuller as product code 3166. The adhesive may be applied by any known process, for example slot coating or by a bead of molten adhesive falling by gravity on the substrate, or adhesive printing. The adhesive may also be applied in one or more spiral pattern by one or more nozzles as is known in the art. The adhesive may be applied first to the backsheet or more advantageously to the topsheet side of the combined topsheet and nonwoven barrier material before the topsheet and backsheet are adhesively joined.

The adhesive may be applied at a basis weight ranging for example from 1 gsm to 30 gsm, taken into account that a higher basis weight will be generally more effective but more costly. A good compromise may by a basis weight for the application of from 5 gsm to 20 gsm, for example 15 gsm. The adhesive may be applied continuously in the longitudinal direction as represented in the Figures, but it is not excluded that the adhesive is applied discontinuously (i.e. intermittently), for example as broken lines.

Figure 5:
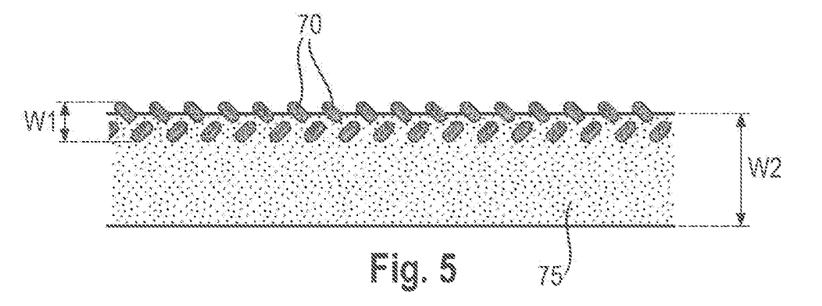
FIGS. 5 and 6 each shows the view of FIG. 4 wherein the adhesive application area has been notionally laterally shifted by a distance of 4 mm laterally in opposite direction.
Figure 6:
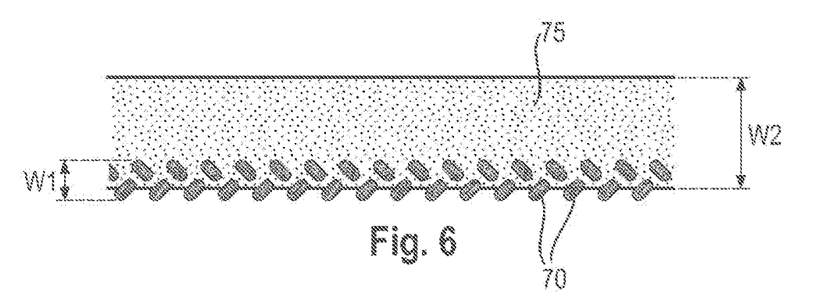

A simple way to achieve a sufficient area of coverage is to provide a continuous line (also called "slot") of adhesive sufficiently large so that even with a shift of up to 4 mm the adhesive area will cover at least 20% of the bonding zone. This is schematically illustrated in FIGS. 4-6. In this case, if the bonding zone has a width W1 superior to 16 mm, it is generally enough that the adhesive application area has a width W2 of at least 25% of W1 to achieve the desired coverage because the possible lateral shift will be negligible relative to the width of the adhesive line. However if the bonding zone, as will typically be the case, has a width W1 which is below 16 mm, the width of the line or band of adhesive should be in larger than the width of the bonding zone. This is for example illustrated in FIG. 4, where the width of the single band of adhesive is much larger than the width of the bonding zone to accommodate a shift of 4 mm in one lateral direction or the other (FIG. 5 and FIG. 6). In particular it may then be advantageous that W2 is at least equal to 8−W1/2 (expressed in mm). For example if W1 is equal to 3 mm, W2 may be advantageously at least equal to 6.5 mm (=8−3/2).

As can be seen using a single line of adhesive can be relatively wasteful of adhesive for the purpose of providing a seal of 20% of the bonding area taking into account the possible lateral shift of 4 mm, as the adhesive width W2 should be in many case much larger than the bonding zone width W1.

Figure 7:
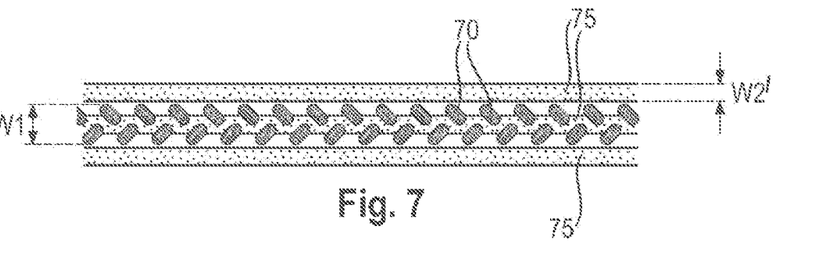
FIG. 7 shows a top view of an exemplary embodiment wherein the adhesive application area comprises three stripes having each a width at least equal to 20% of the width of bonding area.
Figure 8:
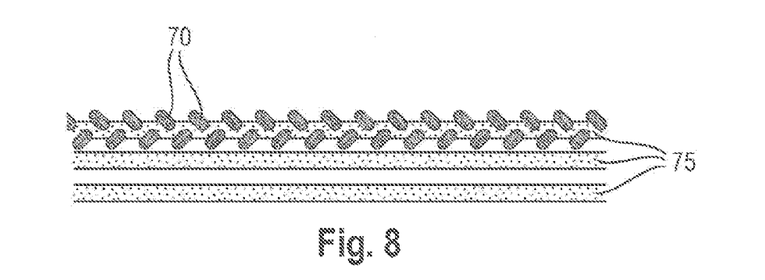
FIGS. 8 and 9 each shows a top view of the embodiment of FIG. 7 wherein the adhesive application area has been notionally laterally shifted by a distance of 4 mm in each lateral direction.
Figure 9:
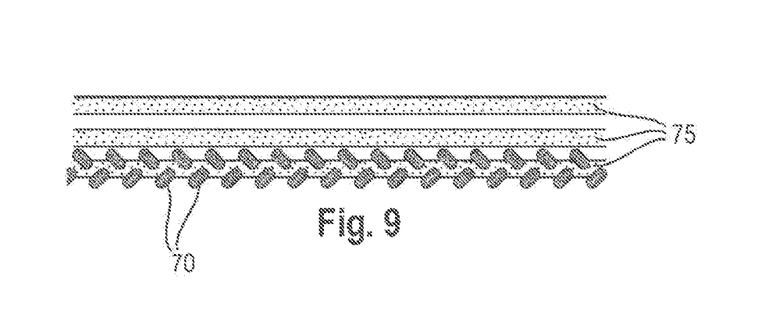

A more economical solution may be to provide an adhesive application area in the form of plurality of longitudinally extending lines 75' of adhesive, in particular two, three or more lines, as shown in FIG. 7. These lines may be typically straight, but it is not excluded that the lines may be curved, for example sinusoidal. In an embodiment, each line may have a width W2' equals to at least 20% of the width W1, and each line is spaced from the adjacent line other by a distance of equal or less than 4 mm so that at least one of the lines of adhesive covers the bonding area when the adhesive application area is notionally shifted laterally left or right by a distance up to 4 mm. Such an embodiment is exemplified in FIGS. 7-9, where the adhesive application area takes the form of three adhesive lines each having a width W2' equal to about a third of the width of the bonding zone W1 and each spaced by a distance of about one third of W1 (for example W2'=1 mm, W1=3 mm and the distance between each adhesive line is 2 mm). The central line is laterally centered on the bonding zone, so that when there is no or only a small lateral shift the central line alone provides a bonding coverage of more than 20% of the surface of the bonding zone. When the shift is higher and up to 4 mm, the central line will in some cases be outside the bonding area, but as illustrated in FIG. 8 and FIG. 9 then at least one of the lateral line will be present in the bonding area and provide the required coverage of at least 20% of the bonding zone. In another embodiment, a plurality of lines may be used so that at least two lines are covering the bonding area simultaneously, even in case of a lateral shift of up to 4 mm in that case each line may have a width W2' that is less than 20% of the width W1 of the bonding area, as long the number of lines covering the bonding area is sufficient to provide the required coverage.

The plurality of adhesive lines have been discussed and shown having the same width W2' but it is not excluded that they may have different widths. At least one line of adhesive may have a minimum width W2' at least equal to 0.4 mm.

Figure 10:
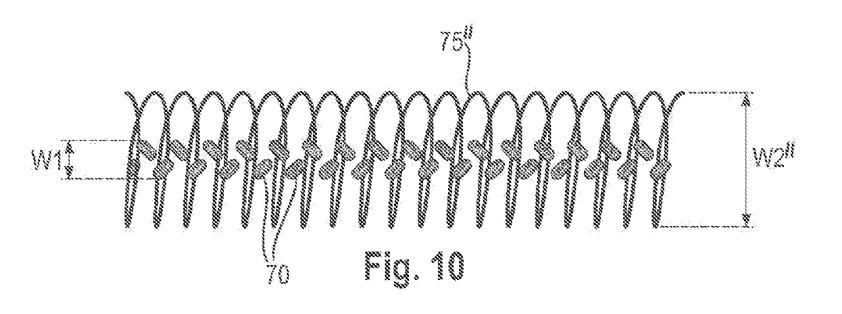
FIGS. 10 and 11 each shows a top view of an attachment area wherein the adhesive application area has the form of one, respectively three, spirals.
Figure 11:
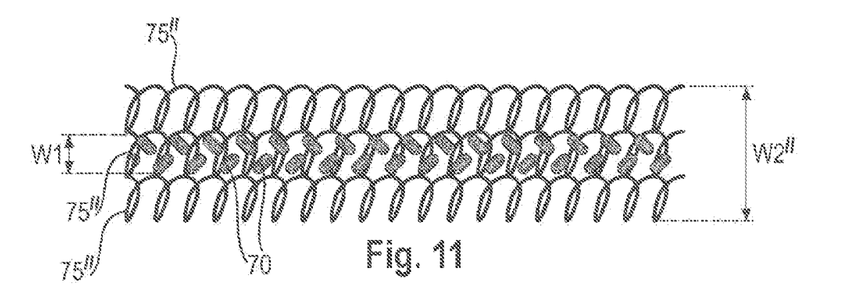

Another exemplary solution is when the adhesive comprises one or more longitudinal extending spiral(s) of adhesive 75" as shown in FIG. 10 or FIG. 11. The thickness (i.e. the width of the adhesive viewed from the top) of the adhesive line forming the spiral and the number of loops per unit or length can be adjusted to provide the required coverage. The thickness of the line may for example vary in the range of from 0.1 mm to 2 mm. The spiral pattern formed by the one spiral or the plurality of adhesive spirals may for example have a width W2" equal to at least 200% of W1 or at least 300% of W1. The spiral or spirals may feature at least 100 loops per meter, in particular at least 200 loops per meter.

Topsheet 24

The topsheet 24 is typically the uppermost part of the absorbent article which is closest and directly in contact with the wearer's skin. The topsheet is preferably compliant, soft-feeling, and non-irritating to the wearer's skin. Further, at least a portion of the topsheet is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet includes fibers, the fibers may be spunbond, carded, wet-laid, meltblown, hydroentangled, or otherwise processed as is known in the art, in particular spunbond PP nonwoven. A suitable topsheet comprising a web of staple-length polypropylene fibers is manufactured by Veratec, Inc., a Division of international Paper Company, of Walpole, Mass. under the designation P-8.

Suitable formed film topsheets are also described in U.S. Pat. No. 3,929,135, U.S. Pat. No. 4,324,246, U.S. Pat. No. 1,342,314, U.S. Pat. No. 1,463,045, and U.S. Pat. No. 5,006,391, Other suitable topsheets may be made in accordance with U.S. Pat. Nos. 4,609,518 and 4,629,643 issued to Curro et al. Such formed films are available from The Procter & Gamble Company of Cincinnati, Ohio as "DRI-WEAVE" and from Tredegar Corporation, based in Richmond, Va., as "CLIFF-T".

Any portion of the topsheet may be coated with a lotion as is known in the art. Examples of suitable lotions include those described in U.S. Pat. No. 5,607,760, U.S. Pat. No. 5,609,587, U.S. Pat. No. 5,635, U.S. Pat. No. 5,643,588, U.S. Pat. No. 5,968,025 and U.S. Pat. No. 6,716,441. The topsheet may also include or be treated with antibacterial agents, some examples of which are disclosed in PCT Publication WO 95/24173. Further, the topsheet, the backsheet or any portion of the topsheet or backsheet may be embossed and/or matte finished to provide a more cloth like appearance.

The topsheet may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 cm$^2$ and about 50 cm$^2$, in particular between about 15 cm$^2$ and 35 cm$^2$. Examples of apertured topsheet are disclosed in U.S. Pat. No. 6,632,501, assigned to BBA NONWOVENS SIMPSONVILLE. WO2011/63582 also discloses suitable colored topsheet having a basis weight of from 12 to 18 gsm and comprising a plurality of bonded points. Each of the bonded points has a surface area of from 2 mm$^2$ to 5 mm$^2$ and the cumulated surface area of the plurality of bonded points is from 10 to 25% of the total surface area of the topsheet.

Typical diaper topsheets have a basis weight of from about 8 gsm to about 30 gsm, in particular between from about 12 to about 18 gsm but other basis weights are possible.

In addition to the adhesive joining the topsheet to the backsheet and providing a coverage of at least 20% of the bondina area formed by the plurality of mechanical and/or heat bonds, the topsheet can be further joined to the backsheet, the absorbent core 28 and/or any other layers using any conventional techniques such as adhesive or mechanical bonding as is known in the art. The topsheet may also extend partially or completely in the gasketing cuffs and be adhesively attached to one or more of the elastic elements 33 in the gasketing cuffs. Usually, the topsheet 24 and the backsheet 25 are joined directly to each other in some locations (e.g. on or close to the periphery of the article) and are indirectly joined together in other locations by directly joining them to one or more other elements of the article such as the absorbent core 28 and acquisition system 50.

Backsheet 25

The backsheet 25 is generally the layer of the article 20 forming the garment-facing surface of the article opposed to its body-facing surface. The backsheet is typically positioned adjacent the absorbent core 28. The backsheet prevents the exudates absorbed and contained therein from soiling articles such as bedsheets and undergarments. The backsheet is typically impermeable to liquids (e.g. urine). The backsheet may for example be or comprise a thin plastic film such as a thermoplastic film having a thickness of about 0.012 mm to about 0.051 mm Exemplary backsheet films include those manufactured by Tredegar Corporation, based in Richmond, Va., and sold under the trade name CPC2 film. Other suitable backsheet materials may include breathable materials which permit vapors to escape from the article while still preventing exudates from passing through the backsheet. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E.I. DuPont; U.S. Pat. No. 5,938,648 to LaVon et al., U.S. Pat. No. 4,681,793 to Unman et al., U.S. Pat. No. 5,865,823 to Curro; and U.S. Pat. No. 5,571,096 to Dobrin et al, U.S. Pat. No. 6,946,585B2 to London Brown, In addition to the adhesive described above, the backsheet may be joined to the topsheet, the absorbent core or any other element of the article by any additional attachment means known in the art. For example, the attachment means may include a uniform continuous layer of adhesive, a patterned layer of adhesive, or an array of separate lines, spirals, or spots of adhesive. Suitable attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. No. 3,911,173, U.S. Pat. No. 4,785,996; and U.S. Pat. No. 4,842,666. Adhesives which have been found to be satisfactory are manufactured by H.B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

Absorbent Core 28

The article of the invention comprises an absorbent core between the topsheet and the backsheet. As used herein, the term "absorbent core" refers to the individual component of the article having the most absorbent capacity and comprising an absorbent material and a core wrap enclosing the absorbent material. The term "absorbent core" does not include the acquisition-distribution system or layer or any other component of the article which is not either integral part of the core wrap nor placed within the core wrap. The core may consist essentially of, or consist of, a core wrap, absorbent material as defined below and glue enclosed within the core wrap. The absorbent core of the invention may generally be of any type, commercially available or only described in the literature.

By "absorbent material" it is meant a material which has some absorbency property or liquid retaining properties, such as SAP, cellulosic fibers as well as synthetic fibers. Typically, glues used in making absorbent cores have no absorbency properties and are not considered as absorbent material.

The absorbent cores may typically comprise, as is known in the art, cellulose pulp mixed with superabsorbent polymers (herein abbreviated as "SAP"), typically with a mass percentage of from 40% to 60% by weight. The absorbent core may also comprise an absorbent material with a higher amount of superabsorbent polymers enclosed within a core wrap. The SAP content may for example represents at least 80% by weight of the absorbent material contained in the core wrap. The core wrap is not considered as absorbent material for the purpose of assessing the percentage of SAP in the absorbent core. The absorbent core may also comprise cellulose pulp only or superabsorbent polymers only as absorbent material.

Cores comprising relatively high amount of SAP with various core designs have been proposed in the past, see for example in U.S. Pat. No. 5,599,335 (Goldman), EP 1,447,066 (Busam), WO 95/11652 (Tanzer), US 2008/0312622A1 (Hundorf), WO 2012/052172 (Van Malderen), WO 2012/170808, WO 2012/170781 (both to Kreuzer), WO 2012/170779, WO 2012/170778 (both to Rosati).

The SAP content may be higher than 80%, for example at least 85%, at least 90%, at least 95% and even up to and including 100% of the weight of the absorbent material contained within the core wrap. This provides a relatively thin core compared to conventional core typically comprising between 40-60% SAP and high content of cellulose fibers. The absorbent material may in particular comprises less than 10% weight percent of natural or synthetic fibers, or less than 5% weight percent, or even be substantially free of natural and/or synthetic fibers. The absorbent material may advantageously comprise little or no airfelt (cellulose) fibers, in particular the absorbent core may comprise less than 15%, 10%, 5% airfelt (cellulose) fibers by weight of the absorbent core, or even be substantially free of cellulose fibers.

Typically the absorbent material (in particular the SAP) will be advantageously distributed in higher amount towards the front edge than towards the back edge as more absorbency is required at the front.

The core wrap may be formed by two nonwoven material 16, 16' which may be at least partially sealed along the edges of the absorbent core. The core wrap may be at least partially sealed along its front edge, back edge and two longitudinal edges so that substantially no absorbent material leaks out of the absorbent core wrap.

The absorbent core of the invention may further comprise adhesive for example to help immobilizing the SAP within the core wrap and/or to ensure integrity of the core wrap, in particular when the core wrap is made of two or more substrates. The core wrap will typically extend to a larger area than strictly needed for containing the absorbent material within. The absorbent core advantageously achieve an SAP loss of no more than about 70%, 60%, 50%, 40%, 30%, 20%, 10% according to the Wet Immobilization Test described in WO 2010/0051166A1.

The absorbent material may be a continuous layer present within the core wrap. In other embodiments, the absorbent material may be comprised of individual pockets or stripes of absorbent material enclosed within the core wrap. In the first case, the absorbent material may be for example obtained by the application of a single continuous layer of absorbent material. The continuous layer of absorbent material, in particular of SAP, may also be obtained by combining two absorbent layers having discontinuous absorbent material application pattern wherein the resulting layer is substantially continuously distributed across the absorbent particulate polymer material area, as taught in US 2008/0312622A1 (Hundorf) for example. The absorbent core 28 may for example comprise a first absorbent layer and a second absorbent layer, the first absorbent layer comprising a first substrate 16 and a first layer of absorbent material, which may be 100% SAP, and the second absorbent layer comprising a second substrate 16' and a second layer of absorbent material, which may also be 100% SAP, and a fibrous thermoplastic adhesive material at least partially bonding each layer of absorbent material to its respective substrate.

The fibrous thermoplastic adhesive material may be at least partially in contact with the absorbent material in the land areas and at least partially in contact with the substrate layer in the junction areas. This imparts an essentially three-dimensional structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% SAP.

Superabsorbent Polymer (SAP)

"Superabsorbent polymers" ("SAP") as used herein refer to absorbent material which are cross-linked polymeric materials that can absorb at least 10 times their weight of an aqueous 0.9% saline solution as measured using the Centrifuge Retention Capacity (CRC) test (EDANA method WSP 241.2-05E). The SAP used may in particular have a CRC value of more than 20 g/g, or more than 24 g/g, or of from 20 to 50 g/g, or from 20 to 40 g/g, or 24 to 30 g/g. The SAP useful in the present invention include a variety of water-insoluble, but water-swellable polymers capable of absorbing large quantities of fluids.

The superabsorbent polymer can be in particulate form so as to be flowable in the dry state. Typical particulate absorbent polymer materials are made of poly(meth)acrylic acid polymers. However, e.g. starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and or surface cross-linked. Suitable materials are described in the PCT Patent Application WO 07/017598 or for example WO 07/046052 or for example WO 2009/155265 and WO 2009/155264. In some embodiments, suitable superabsorbent polymer particles may be obtained by current state of the art production processes as is more particularly as described in WO 2006/083584. The superabsorbent polymers are preferably internally cross-linked, i.e. the polymerization is carried out in the presence of compounds having two or more polymerizable groups which can be free-radically copolymerized into the polymer network. Useful crosslinkers include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in DE-A 103 31 450, mixed acrylates which, as well as acrylate groups, include further ethylenically unsaturated groups, as described in DE-A 103 31 456 and DE-A 103 55 401, or crosslinker mixtures as described for example in DE-A 195 43 368, DE-A 196 46 484, WO90/15830 and WO02/32962 as well as cross-linkers described in WO2009/55265.

The SAP useful for the present invention may be of numerous shapes. The term "particles" refers to granules, fibers, flakes, spheres, powders, platelets and other shapes and forms known to persons skilled in the art of superabsorbent polymer particles. In some embodiments, the SAP particles can be in the shape of fibers, i.e. elongated, acicular superabsorbent polymer particles. In those embodiments, the superabsorbent polymer particles fibers have a minor dimension (i.e. diameter of the fiber) of less than about 1 mm, usually less than about 500 μm, and preferably less than 250 μm down to 50 μm. The length of the fibers is preferably about 3 mm to about 100 mm. The fibers can also be in the form of a long filament that can be woven.

Typically, SAP are spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 μm, or from 50 to 850 μm, preferably from 100 to 710 μm, more preferably from 150 to 650 μm, as measured according to EDANA method WSP 220.2-05. SAP having a relatively low particle size help to increase the surface area of the absorbent material which is in contact with liquid exudates and therefore support fast absorption of liquid exudates.

The SAP may have a particle sizes in the range from 45 μm to 4000 μm, more specifically a particle size distribution within the range of from 45 μm to about 2000 μm, or from about 100 μm to about 1000, 850 or 600 μm. The particle size distribution of a material in particulate form can be determined as it is known in the art, for example by means of dry sieve analysis (EDANA 420.02 "Particle Size distribution).

The absorbent core will typically comprise only one type of SAP, but it is not excluded that a blend of SAPs may be used. The fluid permeability of a superabsorbent polymer can be quantified using its Urine Permeability Measurement (UPM) value, as measured in the test disclosed European patent application number EP12174117.7. The UPM of the SAP may for example be of at least $10 \times 10^{-7}$ $cm^3 \cdot sec/g$, or at least $30 \times 10^{-7}$ $cm^3 \cdot sec/g$, or at least $50 \times 10^{-7}$ $cm^3 \cdot sec/g$, or more, e.g. at least 80 or $100 \times 10^{-7}$ $cm^3 \cdot sec/g$. The flow characteristics can also be adjusted by varying the quantity and distribution of the SAP used in the second absorbent layer.

For most absorbent articles, the liquid discharge occurs predominately in the front half of the article, in particular for diaper. The front half of the article (as defined, by the region between the front edge and a transversal line placed at a distance of half L from the front or back edge may therefore comprise most of the absorbent capacity of the core. Thus, at least 60% of the SAP, or at least 65%, 70%, 75% or 80% of the SAP may be present in the front half of the absorbent article, the remaining SAP being disposed in the back half of the absorbent article.

The total amount of SAP present in the absorbent core may also vary according to expected user. Diapers for newborns may require less SAP than infant or adult incontinence diapers. The amount of SAP in the core may be for example comprised from about 5 to 60 g, in particular from 5 to 50 g. The average SAP basis weight within the (or "at least one", if several are present) deposition area 8 of the SAP may be for example of at least 50, 100, 200, 300, 400, 500 or more g/m². The areas of the channels present in the absorbent material deposition area 8 are deduced from the absorbent material deposition area to calculate this average basis weight.

Core Wrap 16, 16'

The core wrap may be made of a single substrate folded around the absorbent material, or may advantageously comprise two (or more) substrates which are attached to another. Typical attachments are the so-called C-wrap and/or sandwich wrap. In a C-wrap, as exemplarily shown in FIG. 2, the longitudinal and/or transversal edges of one of the substrate are folded over the other substrate to form flaps. These flaps are then bonded to the external surface of the other substrate, typically by gluing.

The core wrap may be formed by any materials suitable for receiving and containing the absorbent material. Typical substrate materials used in the production of conventional cores may be used, in particular paper, tissues, films, wovens or nonwovens, or laminate of any of these. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US 2011/0268932A1, US 2011/0319848A1 or US2011/0250413A1. Nonwoven materials provided from synthetic fibers may be used, such as PE, PET and in particular PP.

If the core wrap comprises a first substrate 16 and a second substrate 16' these may be made of the same type of material, or may be made of different materials or one of the substrate may be treated differently than the other to provide it with different properties. As the polymers used for nonwoven production are inherently hydrophobic, they are preferably coated with hydrophilic coatings if placed on the fluid receiving side of the absorbent core. It is advantageous that the top side of the core wrap, i.e. the side placed closer to the wearer in the absorbent article, be more hydrophilic than the bottom side of the core wrap. A possible way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. An alternative possible way to produce nonwovens with durably hydrophilic coatings is to coat the nonwoven with hydrophilic nanoparticles, e.g. as described in WO 02/064877.

The core wrap may also be formed by a single substrate which may enclose as in a parcel wrap the absorbent material and be for example sealed along the front side and back side of the core and one longitudinal seal, Absorbent Material Deposition Area 8

The absorbent material deposition area 8 can be defined by the periphery of the layer formed by the absorbent material 60 within the core wrap, as seen from the top side of the absorbent core. The absorbent material deposition area 8 can take various shapes, in particular display a so-called "dog bone" or "hour-glass" shape, which shows a tapering along its width towards the middle or "crotch" region of the core. In this way, the absorbent material deposition area may have a relatively narrow width in an area of the core intended to be placed in the crotch region of the absorbent article. This may provide for example better wearing comfort. The absorbent material deposition area 8 may thus have a width (as measured in the transversal direction) at its narrowest point which is less than about 100 mm, 90 mm, 80 mm, 70 mm, 60 mm or even less than about 50 mm. This narrowest width may further be for example at least 5 mm, or at least 10 mm, smaller than the width of the deposition area at its largest point in the front and/or back regions of the deposition area 8. The absorbent material deposition area 8 can also be generally rectangular, for example as shown in FIG. 1, which may be easier to make than other shaped cores.

The absorbent material may be deposited using known techniques, which may allow relatively precise deposition of SAP at relatively high speed. In particular the SAP printing technology as disclosed for example in US 2006/24433 (Blessing), US 2008/0312617 and US 2010/0051166A1 (both to Hundorf et al.) may be used. This technique uses a printing roll to deposit SAP onto a substrate disposed on a grid of a support which may include a plurality of cross bars extending substantially parallel to and spaced from one another so as to form channels extending between the plurality of cross-bars. This technology allows high-speed and precise deposition of SAP on a substrate. The channels of the absorbent core can be formed for example by modifying the pattern of the grid and receiving drums so that no SAP is applied in certain areas to form absorbent material free areas in the form of channels. EP application number 11169396.6 discloses this modification in more details.

Channels 26, 26'

The absorbent material deposition area 8 may optionally comprise at least one channel 26, which is at least partially oriented in the longitudinal direction of the article 80, as exemplarily represented in FIG. 1 and FIG. 2. If the following the plural form "channels" will be used to mean "at least one channel". The channels may have a length projected on the longitudinal axis 80 of the article that is at least 10% of the length L of the article. The channels may be formed in various ways. For example the channels may be formed by zones within the absorbent material deposition area which may be substantially free of absorbent material, in particular SAP. In addition or alternatively, the channel(s) may also be formed by continuously or discontinuously bonding the top side of the core wrap to the bottom side of the core wrap through the absorbent material deposition area. The channels may be advantageously continuous but it is not excluded that the channels are intermittent. Examples of absorbent core comprising channels are disclosed in WO 2012/170808, WO 2012-170781 (both to Kreuzer), WO 2012/170779, WO 2012/170778 (both to Rosati). The acquisition-distribution system or any sub-layer between topsheet and absorbent core layer, or another layer of the article, may also comprise channels, which may or not correspond to the channels of the absorbent core.

The channels may in particular be present at least at the same longitudinal level as the crotch point C in the absorbent article, as represented in FIG. 1 with the two longitudinally extending channels 26, 26'. The channels may also extend from the crotch region or be present in the front region and/or in the back region of the article. The absorbent core 28 may also comprise more than two channels, for example at least 3, or at least 4 or at least 5 or at least 6. Shorter channels may also be present, for example in the back region or the front region of the core. The channels may comprise one or more pairs of channels symmetrically arranged relative to the longitudinal axis 80.

The channels may extend substantially longitudinally, which means typically that each channel extends more in the longitudinal direction than in the transverse direction, and typically at least twice as much in the longitudinal direction than in the transverse direction (as measured after projection on the respective axis). In some embodiments there is no completely or substantially transverse channels in the core. Furthermore, in order to reduce the risk of fluid leakages, the longitudinal main channels typically do not extend up to any of the edges of the absorbent material deposition area, and are therefore fully encompassed within the absorbent material deposition area of the core. Typically, the smallest distance between a channel and the closest edge of the absorbent material deposition area is at least 5 mm.

The channels may have a width We along at least part of its length which is at least 2 mm, or at least 3 mm or at least 4 mm, up to for example 20 mm, or 16 mm or 12 mm. The width of the channel may be constant through substantially the whole length of the channel or may vary along its length. When the channels are formed by absorbent material-free zone within the absorbent material deposition area, the width of the channels is considered to be the width of the material free zone, disregarding the possible presence of the core wrap within the channels. If the channels are not formed by absorbent material free zones, for example mainly though bonding of the core wrap through the absorbent material zone, the width of the channels is the width of this bonding.

At least some or all the channels are advantageously permanent channels, meaning their integrity is at least partially maintained both in the dry state and in the wet state. Permanent channels may be obtained by provision of one or more adhesive material, for example the fibrous layer of adhesive material or a construction glue that helps adhering for example a substrate with an absorbent material within the walls of the channel. Permanent channels may be also in particular formed by bonding the upper side and lower side of the core wrap (e.g. first substrate 16 and the second substrate 16') together through the channels. Typically, an adhesive can be used to bond both sides of the core wrap through the channels, but it is possible to bond via other known means, such as pressure bonding, ultrasonic bonding or heat bonding or combination thereof. The core wrap can be continuously bonded or intermittently bonded along the channels. The channels may advantageously remain or become visible at least through the topsheet and/or backsheet when the absorbent article is fully loaded with a fluid.

Acquisition-Distribution System 50

The absorbent articles of the invention may comprise an acquisition-distribution layer or system 50 (herein "ADS"). The function of the ADS is to quickly acquire the fluid and distribute it to the absorbent core in an efficient manner. The ADS may comprise one, two or more layers, which may form a unitary layer or remain discrete layers which may be attached to each other. In the examples below, the ADS comprises two layers: a distribution layer 54 and an acquisition layer 52 disposed between the absorbent core and the topsheet, but the invention is not restricted to this example.

Typically, the ADS will not comprise SAP as this may slow the acquisition and distribution of the fluid. The prior art discloses many type of acquisition-distribution system, see for example WO 2000/59430 (Daley), WO 95/10996 (Richards), U.S. Pat. No. 5,700,254 (McDowall), WO 02/067809 (Graef). The ADS may comprise, although not necessarily, two layers: a distribution layer and an acquisition layer, which will now be exemplified in more details.

Distribution Layer 54

The distribution layer may for example comprise at least 50% by weight of cross-linked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The cross-linked cellulosic fibers provide higher resilience and therefore higher resistance to the first absorbent layer against the compression in the product packaging or in use conditions, e.g. under baby weight. This provides the core with a higher void volume, permeability and liquid absorption, and hence reduced leakage and improved dryness.

Exemplary chemically cross-linked cellulosic fibers suitable for a distribution layer are disclosed in U.S. Pat. No. 5,549,791, U.S. Pat. No. 5,137,537, WO 95/34329 or US2007/118087. Exemplary cross-linking agents include polycarboxylic acids such as citric acid and/or polyacrylic acids such as acrylic acid and maleic acid copolymers. For example, the crosslinked cellulosic fibers may have between about 0.5 mole % and about 10.0 mole % of a C2-C9 polycarboxylic acid cross-linking agent, calculated on a cellulose anhydroglucose molar basis, reacted with said fibers in an intrafiber ester crosslink bond form.

The distribution layer comprising cross-linked cellulose fibers of the invention may comprise other fibers, but this layer may advantageously comprise at least 50%, or 60%, or 70%, or 80%, or 90% or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In another example, the layer may comprise about 68% by weight chemically cross-linked cellulose fibers, about 16% by weight untreated pulp fibers, and about 16% by weight PET fibers. In another example, the layer of cross-linked cellulose fibers may comprise from about 90-100% by weight chemically cross-linked cellulose fibers.

The distribution layer 54 may be a material having a water retention value of from 25 to 60, preferably from 30 to 45, measured as indicated in the procedure disclosed in U.S. Pat. No. 5,137,537.

The distribution layer may typically have an average basis weight of from 30 to 400 $g/m^2$, in particular from 100 to 300 $g/m^2$. The density of the distribution layer may vary depending on the compression of the article, but may be of between 0.03 to 0.15 $g/cm^3$, in particular 0.08 to 0.10 $g/cm^3$ measured at 0.30 psi (2.07 kPa). The distribution layer may also have a profiled basis weight distribution, in particular with a higher basis weight in the front and crotch regions compared to the bottom region of the article.

Acquisition Layer 52

The ADS may comprise an acquisition layer 52. The acquisition layer may be disposed between the distribution layer 54 and topsheet 24. The acquisition layer 52 may typically be or comprise a non-woven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round hollow PET staple fibers (50/50 or 40/60 mix of 6 denier and 9 denier fibers). An exemplary binder is a butadiene/styrene latex. Non-wovens have the advantage that they can be manufactured outside the converting line and stored and used as a roll of material.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co patent applications US 2003/148684 to Cramer et al. and US 2005/008839 to Cramer et al.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). In certain embodiments, the binder may be present in the acquisition layer 52 in excess of about 12%, about 14% or about 16% by weight. SB latex is available under the trade name GENFLO™ 3160 (OMNOVA Solutions Inc.; Akron, Ohio).

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13-15 gsm high wet strength made of cellulose fibers from supplier Havix.

Fastening System 42-44

The absorbent article may include a fastening system. The fastening system can be used to provide lateral tensions about the circumference of the absorbent article to hold the absorbent article on the wearer as is typical for taped diapers. This fastening system is not necessary for training pant article since the waist region of these articles is already bonded. The fastening system usually comprises a fastener such as tape tabs, hook and loop fastening components, interlocking fasteners such as tabs & slots, buckles, buttons, snaps, and/or hermaphroditic fastening components, although any other known fastening means are generally acceptable. A landing zone 44 is normally provided on the front waist region for the fastener 42 to be releasably attached. Some exemplary surface fastening systems are disclosed in U.S. Pat. No. 3,848,594, U.S. Pat. No. 4,662,875, U.S. Pat. No. 4,846,815, U.S. Pat. No. 4,894,060, U.S. Pat. No. 4,946,527, U.S. Pat. No. 5,151,092 and U.S. Pat. No. 5,221,274 issued to Buell. An exemplary interlocking fastening system is disclosed in U.S. Pat. No. 6,432,098. The fastening system may also provide a means for holding the article in a disposal configuration as disclosed in U.S. Pat. No. 4,963,140 issued to Robertson et al.

The fastening system may also include primary and secondary fastening systems, as disclosed in U.S. Pat. No. 4,699,622 to reduce shifting of overlapped portions or to improve fit as disclosed in U.S. Pat. No. 5,242,436, U.S. Pat. No. 5,499,978, U.S. Pat. No. 5,507,736, and U.S. Pat. No. 5,591,152.

Front and Back Ears 46, 40

The absorbent article may comprise front ears 46 and back ears 10 as is known in the art. The ears can be integral part of the chassis, for example formed from the topsheet and/or backsheet as side panel. Alternatively, as represented on FIG. 1, they may be separate elements attached by gluing with an adhesive applied as a slot or spiral and/or heat embossing or pressure bonding. The back ears 40 are advantageously stretchable to facilitate the attachment of the tabs 42 on the landing zone 40 and maintain the taped diapers in place around the wearer's waist. The back ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Elastic Waist Feature

The absorbent article may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 28 and generally forms at least a portion of the end edge of the absorbent article. Disposable diapers can be constructed so as to have two elastic waist features, one positioned in the front waist region and one positioned in the back waist region. The elastic waist feature may be constructed in a number of different configurations including those described in U.S. Pat. No. 4,515,595, U.S. Pat. No. 4,710,189, U.S. Pat. No. 5,151,092 and U.S. Pat. No. 5,221,274.

Relations Between the Layers

Typically, adjacent layers and components will be joined together using conventional bonding method such as adhesive coating via slot coating or spraying on the whole or part of the surface of the layer, or thermo-bonding, or pressure bonding or combinations thereof. This bonding is not represented in the Figures (except for the bonding zone and the adhesive application area) for clarity and readability but bonding between the layers of the article should be considered to be present unless specifically excluded. Adhesives may be typically used to improve the adhesion of the different layers, for example between the backsheet and the core wrap. It is not excluded that a background glue, such as a spiral glue, is used over the whole of the backsheet and thus further attaches the backsheet to the topsheet at the periphery (sides, front and back) of the article. The glue may be any standard hotmelt glue as known in the art.

Method of Making the Articles

The articles described above may be made by any suitable methods. In an on-line making process, the machine-direction (MD) may typically be parallel to the longitudinal axis 80 of the article, and the cross-direction (CD) parallel to the lateral axis 90. A particular method may comprise the steps of:

attaching the web of nonwoven barrier material 110 to the topsheet by a plurality of mechanical and/or heat bonds 70 at least in the crotch region of the absorbent article, the plurality of mechanical and/or heat bonds defining a longitudinally extending bonding area 71 having a width W1; and attaching the backsheet to the topsheet at least in the crotch region of the absorbent article by applying an adhesive between these layers.

The adhesive may have a target application area such that the adhesive covers at least 20% of the bonding area 70 between the topsheet and web of nonwoven barrier material when the adhesive is applied without lateral shift. The adhesive can be further applied in a pattern such that the required coverage in the actual adhesive deposition area is also present when the adhesive application process presents a lateral tolerance of at least of up to 4 mm in the lateral direction (i.e. left or right when the article is orientated as on FIG. 1).

The step of attaching the web of nonwoven barrier material to the topsheet may advantageously take place before the step of attaching the backsheet to the topsheet, so that the adhesive contacts directly the mechanical and/or heat bonding area 71 when these layers are attached. The adhesive may be applied to any of the layers to be attached, but may be advantageously applied to the already attached topsheet/non woven barrier material web, typically on the topsheet side. This may reduce lateral variability compared to applying the adhesive to the backsheet. The target application area may be advantageously laterally centered on the mechanical bonding area.

The rest of absorbent articles may be assembled by any conventional methods known in the art. In particular the articles may be hand-made, or industrially produced at high speed. The topsheet 24, the backsheet 25, the absorbent core 28 and the other article components may be assembled in a variety of well known configurations, in particular by gluing, mechanical bonding, heat embossing and combinations thereof. Exemplary diaper configurations are described generally in U.S. Pat. No. 3,860,003, U.S. Pat. No. 5,221,274, U.S. Pat. No. 5,554,145, U.S. Pat. No. 5,569,234, U.S. Pat. No. 5,580,411, and U.S. Pat. No. 6,004,306.

EXPERIMENTAL

The values indicated herein are measured according to the methods indicated herein below, unless specified otherwise. All measurements are performed at 21±2° C. and 50±20% RH, unless specified otherwise. All samples should be kept at least 24 hours in these conditions to equilibrate before conducting the tests, unless indicated otherwise.

Holes Formation Assessment

The following materials were combined using mechanical bonding with a bonding pattern having staggered ovoid bonds with a shape as represented in the Figures. The width W1 of the mechanical bonding area was about 3 mm. The material tested were PP based:

B: a 12 gsm white Spunbond web, supplied by Polymer Group Inc (PGI);

C: a 13 gsm SMS (6/1/6) material, supplied by PGI;

D: a 22 gsm spunbond material, supplied by Fiberweb Washogal;

F: a 30 gsm Highly Extensible SpunBond material (HESB) supplied by First Quality Nonwovens;

G: a 13 gsm SMNS (5.5/1/1/5.5) material with a N-fiber layer (made on a pilot line).

Materials C, F and G are suitable as topsheet (after being treated with a surfactant to become hydrophilic), while materials B, D and F are suitable as a nonwoven barrier material for the barrier leg cuffs.

The resulting mechanical bonds were examined using a camera and a software imaging system to measure the amount of holes and the number of bonds comprising a hole. The number of holes and the percentage of bonds with hole were normalized to correspond to one meter of bonded materials.

| Condition | Total gsm | # of holes (>1 pixel) | % of bonds with hole (>1 pixel) | Largest hole (pixel) |
|---|---|---|---|---|
| F + F | 60 | 0 | 0.0% | 0 |
| C + F | 43 | 16 | 0.1% | 14 |
| G + F | 43 | 18 | 0.1% | 10 |
| G + D | 35 | 105 | 0.8% | 29 |
| C + D | 35 | 67 | 0.3% | 31 |
| C + B | 25 | 891 | 5.8% | 59 |
| G + B | 25 | 1027 | 7.0% | 79 |

As can be seen, for all material combinations having a basis weight of less than 50 gsm, micro to macro holes were formed in the bonding area. The inventors surprisingly observed that even under laboratory controlled condition, it was impossible to define the right process setting and controls to reliably prevent holes between the nonwoven topsheet and nonwoven cuffs when the combined basis weight was below 50 gsm.

Barrier Function Assessment

The barrier function was evaluated on options with an adhesive seal comprised of three line slots of adhesive laterally centered on the mechanical bonds (similarly to FIG. 7) versus a control sample with slots of adhesive placed outside the Mechanical bonding area. The mechanical bonding was 3 mm wide with a pattern as shown in FIG. 7.

The materials mechanically bonded were a 15 gsm SMS (7/1/7) barrier cuff from First Quality Nonwovens Inc and a 12 gsm hydrophically treated spundbond topsheet from PGI. An adhesive from Fuller (HL-3166) was applied between the mechanical bonded composed barrier cuff and topsheet and a 16 gsm backsheet film material from RKW Group as per the description below.

Sample 1: Control using 5 slots of 10 gsm Fuller adhesive, 1 mm wide applied at 1 nm spacing, outside of the outer edge of the mechanical bonding area (adhesive present but not covering the area W2). The closest slot was at a distance of about 3 mm from the bonding area.

Sample 2: Three slots of 5 gsm Fuller adhesive, 1 mm wide applied at 1 mm spacing from each other, centered below the mechanical bonded area of the composed barrier cuff and topsheet nonwovens and the backsheet film (as in FIG. 7).

Sample 3: Same as sample 2 but with the Fuller adhesive applied at 10 gsm.

The Cuff Barrier Functionality Test measures the amount of a solution (0.9 w. % NaCl with 0.3 w. % Na-Cholate, surface tension of 46.5-49.5 mN/M) that permeates the barrier leg cuff sample in 30 seconds. A 178 mm long strip of the combined barrier cuff, topsheet and backsheet as per the above sample preparation is placed on a 45° in-plane with acrylic holder to maintain the barrier cuff at 90 degrees from the in-plane simulating a fully standing barrier. 60 mL of the Sodium cholate solution is applied above the barrier cuff to reach a height of 26 mm and the amount of solution leaking in 30 s through the barrier cuff is reported.

The amount of solution leaking thorough the cuff in 30 seconds is reported below:

| Sample | Barrier Function Leak in 30 s |
|---|---|
| Sample 1 (Control) | 21.9 g |
| Sample 2 (3 slots of 1 mm at 5 gsm) | 6.1 g |
| Sample 2 (3 slots of 1 mm at 15 gsm) | 3.1 g |

Raising the basis weight of the glue increases the seal function of the seal. However a higher basis weight is also more costly. It is believed that the adhesive lines that are not covering the bonding area are not effective to stop fluid run-off.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for personal hygiene having a body-facing surface and an opposed garment-facing surface, the article having a front region, a back region and an intermediate crotch region, the absorbent article comprising:
   a liquid pervious topsheet;
   a liquid impervious backsheet;
   an absorbent core disposed between the topsheet and the backsheet;
   wherein the absorbent article comprises on each of its longitudinal sides:
   a barrier leg cuff having a free distal edge, and an elastically contractible gasketing cuff disposed adjacent to a longitudinal edge of the absorbent article;
   wherein the gasketing cuff and barrier leg cuff are at least partially formed from the same web of nonwoven barrier material extending at least from the distal edge of the barrier leg cuff to the longitudinal side edge of the article;
   wherein the nonwoven barrier material is attached at least in the crotch region to the topsheet by a plurality of mechanical and/or heat bonds, the plurality of mechanical and/or heat bonds defining in the crotch region a longitudinally extending bonding area having a width W1;
   the absorbent article further comprising an adhesive attaching the topsheet to the backsheet at least in the crotch region;
   wherein the adhesive covers about 20% or more of the bonding area, this being also the case when the adhesive is shifted laterally by any distance of about 4 mm or less;
   wherein the adhesive comprises a plurality of longitudinally extending lines of adhesive, wherein each line has a width W2' equal to about 20% or more of the width W1, and wherein each line is spaced from an adjacent line by a distance equal to about 4 mm or less so that at least one of the lines of adhesive covers the bonding area when the adhesive is shifted laterally by any distance of about 4 mm or less.

2. The absorbent article according to claim 1, wherein the adhesive covers about 50% or more of the bonding area, this being also the case when the adhesive is shifted laterally by any distance of about 4 mm or less.

3. The absorbent article according to claim 1, wherein the adhesive is laterally centered on the bonding area.

4. The absorbent article according to claim 1, wherein the barrier leg cuff comprises an elastic element for spacing the distal edge of the barrier leg cuff away from the body-facing surface of the absorbent article, so as to cause the barrier leg cuff to stand up.

5. The absorbent article according to claim 1, wherein the topsheet and the web of nonwoven barrier material have a combined basis weight of about 60 gsm or less.

6. The absorbent article according to claim 5, wherein the combined basis weight is in the range of about 10 to about 50 gsm.

7. The absorbent article according to claim 1, wherein the mechanical bonds are generally of ovoid shape, with their longer axis aligned at an angle of from about 20° to about 80° relative to the longitudinal direction of the article.

8. The absorbent article according to claim 7, wherein the mechanical bonds are staggered in chevrons along two parallel lines along the longitudinal direction of the article.

9. The absorbent article according to claim 1, wherein the width W1 ranges from about 0.5 mm to about 10 mm.

10. The absorbent article according to claim 1, wherein the bonding area and the adhesive extend longitudinally beyond the crotch region into the front region and back region of the absorbent article.

11. The absorbent article according to claim 1, wherein the plurality of mechanical and/or heat bonds extend longitudinally beyond the crotch region into the front region and back region of the absorbent article.

12. The absorbent article according to claim 1, wherein the absorbent core comprises from about 80% to about 100% by weight of superabsorbent polymers as absorbent material.

13. The absorbent article according to claim 1, wherein the absorbent core comprises at least a pair of channels free of absorbent material.

* * * * *